United States Patent
Cherwonogrodzky et al.

(10) Patent No.: US 6,436,652 B1
(45) Date of Patent: Aug. 20, 2002

(54) METHOD OF DETECTING A PATHOGEN USING A VIRUS

(75) Inventors: John W. Cherwonogrodzky, Medicine Hat; Kamil Lotfali, West Vancouver, both of (CA)

(73) Assignee: Her Majesty the Queen in right of Canada, as represented by the Minister of National Defence of Her Majesty's Canadian Government, Ottawa (CA)

(*) Notice: Subject to any disclaimer, the term of this patent is extended or adjusted under 35 U.S.C. 154(b) by 0 days.

(21) Appl. No.: 09/376,288

(22) Filed: Aug. 18, 1999

Related U.S. Application Data

(62) Division of application No. 08/514,096, filed on Aug. 11, 1995, now Pat. No. 6,355,445.

(30) Foreign Application Priority Data

Aug. 12, 1994 (CA) ............................................ 2130072

(51) Int. Cl.⁷ .................... G01N 33/554; G01N 33/563; A61K 38/54; A61K 39/12
(52) U.S. Cl. .................. 435/7.32; 424/94.3; 424/184.1; 424/193.1; 424/204.1; 424/252.1; 435/7; 435/188; 436/512; 436/527; 436/538
(58) Field of Search ...................... 435/7, 7.32, 172.1, 435/188; 436/512, 527, 538; 424/184.1, 193.1, 204.1, 252.1, 94.3

(56) References Cited

U.S. PATENT DOCUMENTS

| | | | |
|---|---|---|---|
| 4,104,126 A | 8/1978 | Young | 195/103.5 |
| 4,657,853 A | 4/1987 | Freytag et al. | 435/7 |
| 4,797,363 A | 1/1989 | Teodoresco et al. | 435/235 |
| 5,310,649 A | 5/1994 | Ficht et al. | 435/6 |

FOREIGN PATENT DOCUMENTS

| | | | |
|---|---|---|---|
| CA | 1 212 051 | 9/1986 | A61K/39/10 |

OTHER PUBLICATIONS

Eder et al, Structural and functional comparison of antibodies to common and specific determinants of papain and chymopapain. Immunochemistry, vol. 10, pp. 535–543, Mar. 1973.*

Ausubel et al. Current Protocols in Molecular Biology, Greene Publishing Assoc. And Wiley, Interscience, Toronto, vol. 1(Suppl. 13):, Section 1.11.4(1989).

Avrameas et al., "Coupling of Enzymes to Antibodies and Antigens", Scand. J. Immunol. 8(Suppl.7):7–23(1978).

Chamberlain, "Evaluation of Live Tularemia Vaccine Prepared in a Chemically Defined Medium", Applied Microbiology 13(2):232–235 (1965).

Day, "Sized of Immunoglobulins", Advanced Immunochemistry, Williams & Wilkins Co., Baltimore (1972) p. 93.

Healey et al., "A rapid Semi quantitative Capillary Enzyme Immunoassay for Digoxin", Clinica Chimica Acta. 134:51–58(1983).

Rigby, Chapter 6, "The Brucellaphages", Nielsen and Duncan (ed.) Animal Brucellosis, CRC Press, Boca Raton, pp. 121–130 (1990).

Tortorello et al., "Microtiter Plate Assays for the Measurement of Phage Adsorption and Infection in Lactococcus", Analytical Biochemistry 192:362–366 (1991).

Block et al., "A Phage–Linked Immunoabsorbant System for the Detection of Pathologically Relevant Antigens", Bio Techniques 7(7):756–758 (1989).

Steensma et al., "An Enzyme–linked Immunosorbent Assay (ELISA) for PBS Z1, a Defective Phage of *Bacillus subtilis*", J. gen. Virol. 44:741–746 (1979).

Steensma, H. Y., "Absorption of the Defective Phase PBS Z1 to *Bacillus subtilis* 168 Wt", J. gen. Virol. 52:93–101.

Nielsen et al., "A Review of Enzyme Immunoassay for Detection of Antibody to *Brucella abortus* in Cattle", Veterinary Immunology and Immunopathology 18:331–347 (1988).

Diaz et al., Chapter 6, "Laboratory Techniques in the Diagnosis of Human Brucellosis", Young and Corbel (ed), Brucellosis: Clinical and Laboratory Aspects, CRC Press, Boca Raton, Florida, pp. 73–83 (1989).

Corbel, Michael J., Chapter 5, "Microbiology of the Genus *Brucella*", Brucellosis: Clinical and Laboratory Aspects, pp. 53–72 (1989).

O'Sullivan et al., "Methods for the Preparation of Enzyme–Antibody Conjugates for Use in Enzyme Imunoassay", Methods in Enzymology 73:147–166 (1981).

* cited by examiner

Primary Examiner—Rodney P Swartz
(74) Attorney, Agent, or Firm—Nixon & Vanderhye P.C.

(57) ABSTRACT

A bacteriophage linked to an enzyme can replace an antibody in a system for detecting the presence of a bacteria in a sample. Specifically *Brucella abortus* (a pathogen which causes brucellosis in cattle) can be detected using Brucella bacteriophage for the virus, urease for the enzyme linked to the bacteriophage, m-maleimidobenzoyl-N-hydrosysuccimide ester as a coupling reagent, sera from mice immunized with Brucella bacteriophage for a detector antibody, urease conjugated to anti-mouse sheep antibody for an indicator, and urea with bromcresol purple as the substrate. The materials can be used in indirect (sandwich) or direct enzyme-linked viral assays (ELVirA).

24 Claims, No Drawings

METHOD OF DETECTING A PATHOGEN USING A VIRUS

This is a divisional of application Ser. No. 08/514,096, filed Aug. 11, 1995, now U.S. Pat. No. 6,355,445, the entire content of which is hereby incorporated by reference in this application.

This invention relates to a method of detecting a pathogen using a virus.

More specifically, the invention relates to the detection of the pathogen *Brucella abortus* using the virus Brucella bacteriophage.

Brucellosis is a disease caused by the bacterial genus, Brucella, named after Dr. David Bruce who discovered the organism in 1887. The disease is zoonotic, although different species are usually found in specific domestic animals, such as cattle (*B. abortus*), swine (*B. suis*), sheep (*B. ovis*), goats (*B. melitensis*) and dogs (*B. canis*). The manifestations of these bacteria in animals are usually reproductive complications (aborted fetuses, inflamed uterus or orchitis). While vaccinations in animals have proven partially effective in offering protection, the vaccines are pathogenic for other animals and humans. Infection is passed to humans through the ingestion of milk, milk products, the handling of contaminated carcases or aborted fetuses, and by the contact of infected tissues or body fluids. The disease is rarely passed from human to human, and then usually by exposure to contaminated blood specimens. Brucella is the number one cause of laboratory acquired infection. The great majority of patients with the disease survive, but only a small percentage ever recover completely. Usually the people infected are subject to relapses of recurrent, or undulant, fever, incapacitation, nausea and arthritis.

Brucella is a highly infective organism which causes debilitating symptoms, and which can persist in the environment for months under the right conditions. There are no effective vaccines and only limited therapeutic recourses to the bacteria. In other words, Brucella is potentially a bacterial warfare agent. Accordingly, there is a need for an effective detection assay.

Methods are available for the detection of pathogenic bacteria, but these have limitations. Culturing bacteria from clinical specimens is sensitive but often requires selective media, several days of incubation and the right nutrients or conditions (Brucella needs 5–10% carbon dioxide). Common serological techniques are usually insensitive. The enzyme-linked immunosorbent assay is usually rapid, sensitive and specific but gives false-positive for *Staphylococcus aureus* protein A, requires a source of antibodies which is difficult to raise, and may not detect different strains of the same species.

The object of the present invention is to meet the above defined need for an effective detection assay for Brucella (specifically *Brucella abortus*) in the form of an assay for the detection of pathogenic bacteria by using bacteriophages, a type of virus that is specific for host bacteria.

Accordingly, the present invention relates to a method of detecting the presence of a pathogenic bacteria in a liquid sample using a bacteriophage specific to the bacteria comprising the steps of producing a bacteriophage stock; conjugating the bacteriophage stock to an enzyme; mixing the conjugated bacteriophage with a sample suspected of containing the bacteria; and detecting any changes resulting from a reaction of the conjugated bacteriophage with the bacteria.

More specifically, the invention relates to a method of detecting the presence of the bacteria *Brucella abortus* in a sample using virus Brucella comprising the steps of producing a stock of Brucella bacteriophage, conjugating the Brucella bacteriophage to the enzyme urease; mixing the conjugated Brucella bacteriophage with a sample suspected of containing the bacteria *Brucella abortus*; and detecting any changes resulting from a reaction of the conjugated Brucella bacteriophage with the *Brucella abortus*.

MATERIALS AND METHODS (1) Bacteria and bacteriophages: *Brucella abortus* 30, *B. abortus* 2308, B. melitensis 16M, B. suis 144 and bacteriophages WB1 (Webridge) and BK (Berkeley) were acquired from Agriculture Canada, Animal Diseases Research Institute (ADRI-Nepean), Nepean, Ontario, *Francisella tularensis* LVS was acquired from Dr. F. Jackson, Dept. Medical Bacteriol., University of Alberta, Edmonton, Alberta, who in turn acquired it from the American Type Culture Collection. *Escherichia coli* 1511 was acquired from the Dept. Microbiology & Infectious Diseases, University of Calgary at Calgary, Alberta.

(2) Antibodies: To compare methods of conjugating enzymes to other proteins, antibodies were used as the other protein. Mouse anti-*Brucella abortus* antisera were raised by immunizing mice (100 ug smooth-lipopolysaccharide/0.2 ml/mouse, given on weeks 0, 1, 5 at two sites intramuscular (i.m.) in the thigh and two sites subcutaneous (s.c.) under the skin on the back, blood taken by heart puncture on week 5, sera removed and pooled). Mouse monoclonal antibody Ys-T9-2 (3 mg antibody/ml ascites fluid) was acquired from D. R. Bundle of the National Research Council of Canada. Mouse anti-bacteriophage WB1 antisera were raised by immunization with 0.2 ug bacteriophage/0.2 ml/mouse [in a partially purified preparation that has $1.2 \times 10^9$ plaque forming units, 1 ug bacteriophage protein, and 160 ug total protein (growth medium proteins, *Brucella abortus* lysate debris also present) per ml] given on weeks 0, 1 and 2 both i.m. and s.c. as before, blood was taken on week 3 and the sera removed and pooled. Urease conjugated anti-mouse IgG goat antiserum was from the Sigma Chemical Co. (St. Louis, Mo.).

(3) Antigens: *Brucella abortus* 2308 and *B. melitensis* 16M were grown in Brucella broth (under an atmosphere with a 5% $CO_2$), *Escherichia coli* 1511 was grown in nutrient broth, and *E. tularensis* LVS was grown in Chamberlain's synthetic broth. The cells were killed with 2.0% phenol, removed by centrifugation, tested for sterility, washed in saline, then dispensed into vials so that after lyophilization there was 10 mg/vial.

(4) Chemicals: Urease (type VII), urea substrate tablets and bromcresol purple indicator tablets were obtained from the Sigma Chem. Co., Cesium chloride was obtained from Boehringer Mannheim GmbH, West Germany, and m-maleimidobenzoyl-N-hydroxysuccinimide (MBS) was obtained from Pierce Chemical Co., Rockford, Ill.

*Brucella abortus* Bacteriophage Preparations

Bacteriophages WB1 (Weybridge) and BK (Berkeley) were initially diluted $10^4$ and $10^3$ RTD (routine test dilution, highest dilution producing lysis on the propagating strain). Of the Brucella species and strains tested with both bacteriophages, *B. abortus* 30 was the most sensitive (i.e. the best propagating host) to the bacteriophages, and WB1 appeared more lytic than BK. Bacterial cells grown on agar plates for a day did not appear to be lyzed by a bacteriophage inoculum. Plates that were freshly inoculated with *B. abortus* 30 (a suspension that gave an $O.D._{620}$ of 0.1 and $10^9$ bacteria, a 1:100 dilution of this was made and 0.1 ml of the latter was plated onto Brucella agar plate with crystal violet), then with $10^3$ plaque forming units (PFU), and incubated at 37° C., 5% $CO_2$, showed extensive lysis. Small colonies of resistant bacteria (likely lysogenic) had to be removed. The plaques were cut and removed aseptically with an inoculating needle, placed in 50 ml sterile saline in a 250 ml flask, agitate (150 rpm., 1 h, 37° C.), and the liquid was filtered through a 0.22 um filter.

(a) In the first two attempts to produce a bacteriophage stock, the above described bacteriophage filtrate was simply added to early cultures of B. abortus 30 ($10^8$ bacteria in 2 litres of Brucella broth in a 6 litre flask, 16 h, 37° C., 5% $CO_2$, 150 rpm). The culture was shaken for 24 hours. The bacteria were removed by centrifugation and the supernatant was filtered through a 0.45 um filter (changing after every 250 ml volume). The yield was $3.2\times10^7$ PFU of bacteriophage/ml in 1200 ml.

240 ml (one-fifth of supernatant) of 34% w/v) Carbowax—PEG 6000, 1% dextran sulfate (w/v) 7.5% NaCl (w/v) was added to 1200 ml of culture supernatant to concentrate the phages. The solution was gently mixed and stored overnight at 4° C. Most of the supernatant was poured off, but the bottom 300 ml was centrifuged at 12,000×g, 4° C. for 15 min. The top layer was removed, and to the bottom layer solid KCl was slowly added to make a 1 M solution. This was chilled for 30 min on ice, centrifuged at 12,000×g, 4° C. for 15 min. and this time the supernatant was kept. The supernatant was dialysed against saline, and ultracentrifuge overnight at 100,000×g at 4° C. The supernatant was gently removed, and the tubes were rinsed vigorously with saline. The yield was $5.4\times10^8$ PFU of bacteriophages/ml in 10 ml.

(b) In the next 2 attempts, 20 h cultures of *B. abortus* 30 were centrifuged (Level 3 containment procedures used), the cells were resuspended in 50 ml of a buffer (0.58% NaCl, 0.2% $MgSO_4$. $7H_2O$, 50 mM TRIS-HCl, pH 7.5) which enhanced attachment and infection of the bacteria, the 50 ml bacteriophage preparation was added (incubation was 1 h, 37° C., 150 rpm), and the bacteria-bacteriophage mixture was added to 2 litres of fresh broth. After another 24 h at 37° C. and 150 rpm, the culture was left static for 24 h. The cells were removed by centrifugation and filtration as before. The yield was $5\times10^7$ PFU of bacteriophage/ml in 1700 ml.

In order to concentrate the bacteriophage, the above filtrate was lyophilized, and the solid was redissolved in 40 ml distilled water and then dialysed against 1% saline. The yield was $1.2\times10^9$ PFU of bacteriophage/ml in about 50 ml.

In order to purify the phage, a CsCl step gradient was made with 3.5 ml of A (56.24 g CsCl+43.76 ml water, density 1.7), 2.5 ml of B (45.41 g CsCl+54.59 ml water, density 1.5), 2.5 ml of C (31.24 g CsCl+68.76 ml water, density 1.3), 2 ml of sample, and a topping layer of mineral oil, all in ultra-clear centrifuge tubes for an SW-27 rotor (swinging bucket). Centrifugation was for 2 h at 4° C. and 24,000 rpm. The tubes were then removed, the bottoms were pierced with a 26 gauge needle, and 1 ml fractions were removed. Each fraction was read at an $A_{280\ nm}$, and the first peak (resting on the CsCl B layer) was phage.

Conjugation of Enzymes to Proteins (a) The one-step glutaraldehyde method: (This technique follows that of Avrameas et al., 1978.)

(1) 3 mg or antibody bacteriophage is mixed with 10 mg of urease in 1 ml of 0.1 M sodium phosphate buffer, PB (pH 6.8)

(2) 0.1 ml of 1% glutaraldehyde is slowly added while the mixture is stirring. Stir for an additional 5 minutes and then let sit at room temp (22° C.) for 3 h.

(3) Add 0.1 ml of 1 M lysine at pH 7 to the solution and let it sit at room temp for 2 h.

(4) Dialyze the mixture against 0.01 M phosphate, 0.85% NaCl, pH 7 phosphate buffer saline (PBS).

(5) Centrifuge at 40,000×g, 4° C. for 20 min to remove debris.

(6) Filter through a 0.22 um membrane, add an equal volume of glycerol for stability and store at 4° C.

(b) The two-step glutaraldehyde method: (This technique follows that of Avrameas and Ternynck, 1971)

(1) 10 mg of urease is dissolved in 0.2 ml of 1.25% glutaraldehyde in PB. The solution is incubated for 18 h at 22° C. Excess glutaraldehyde is removed by dialysis or gel filtration. Make to 1 ml final volume.

(2) Dialyze against 0.1 M sodium carbonate buffer (pH 9.5).

(3) Add 0.5 mg of antibody or bacteriophage/0.1 ml saline to the urease solution (make sure pH is above 9). Incubate 24 h at 4° C.

(4) Add 0.1 ml of 0.2 M ethanolamine and incubate for 2 h at 4° C.

(c) The MBS (m-maleimidobenzoyl-N-hydroxysuccinimide) method: (This technique follows that of Healey et al., 1983)

(1) Dimethylformamide was dried over Sephadex beads. 25 mg (8 mM) of MBS was added to the dimethylformamide. 0.1 ml of this was added to 3 mg antibody or bacteriophage in 0.4 ml of PBS. Incubation was for 30 min at 22° C., with continuous gentle swirling.

(2) Unreacted MBS was removed by gel filtration or dialysis.

(3) 6 mg of urease was added, then incubated 2 h at 22° C., with swirling.

(4) 2-mercaptoethanol was added to a final concentration of 2 mM (i.e. 0.1 ml of a 1:100 dilution), and incubation was for 30 min at 22° C., with swirling.

(5) The mixture was dialysed against PBS, filtered through a 0.22 um membrane, an equal volume of glycerol was added, and the mixture was stored at 4° C.

The Enzyme-Linked Viral Assay (ELVirA)

(a) The Direct Method:

(1) 200 ul of bacterial dilutions (50, 10 and 2 ug/ml in 0.06 M carbonate buffer, pH 9.6) were applied to wells of a MaxiSorp Immuno-plate (Nunc InterMed, Denmark). The plate was incubated for 1 h at 37° C.

(2) The microtiter plate was washed 5 times in wash buffer [0.01 M sodium phosphate, 0.85% NaCl (or PBS), 0.05% Tween (trademark), 0.1% bovine serum albumin (BSA), pH 7].

(3) 300 ul of blocking buffer (0.01% Tween, 2% BSA, in PBS) was added to each well, and incubation was for 1 h at 37° C.

(4) The plate was washed 5 times as before.

(5) Because of limited amounts of bacteriophage, a 1 ug concentration was used for the MBS protocol and 200 ul of the urease-conjugated bacteriophage was used without dilution onto the plate. Incubation was for 1 h at 37° C.

(6) The plate was washed 5 times in triple-distilled water.

(7) 200 ul of urease substrate was added, incubated at 37° C., and read every 10 min. The reaction can be followed either by the increase of absorbance at 595 nm, or the decrease of absorbance at 405 nm.

(b) The Indirect (Sandwich) Method:

1) 200 ul of bacterial dilutions were added to the wells, incubated and washed as above.

(2) 300 ul of blocking buffer was added to the wells, incubated and washed.

(3) 200 ul of a bacteriophage preparation (1 ug/ml PBS) were added, incubated and washed.

(4) 200 ul of a 1:5 dilution of anti-bacteriophage mouse antiserum were added, incubated and washed.

(5) 200 ul of a 1:500 dilution of anti-mouse IgG goat urease-conjugated antiserum was added, incubated and washed.

(6) Urease substrate was added. The reaction required 4 h at 37° C. before it could be read at 595 nm.

RESULTS AND DISCUSSION

At first glance, it would appear that antibodies and bacteriophages have very little in common. Antibodies are proteins (e.g. for IgG, two heavy and two light chains linked with sulfhydryl bonds, molecular weight around 160,000) raised by lymphocytes as part of the body's immune deFense. Bacteriophages are viruses (molecular weight over 1,000,000,000) that are made of protein encapsulated nucleic acids and that replicate within bacterial hosts. However, both may interact with a bacterium, the first as part of the body's defence against infection, the latter as a means of replication. Hence several similarities can be seen:

| Antibody | Bacteriophage |
|---|---|
| made of protein | has a protein coat |
| attaches to antigens (unique sequence of compounds) on the bacterial surface | attaches to a receptor (unique sequence of compounds) on the bacterial surface |
| has 2 binding sites called the "variable region" | has a binding site called the "base plate" |
| specificity and binding affinity may vary as in the case of different monoclonal antibodies to the same antigen | specificity and binding affinity may vary with different phages to the same bacterial host |

It is a result of these similarities that the inventors developed a novel detection system that replaced an antibody with a bacteriophage.

As mentioned above, two bacteriophages, WB1 (Weybridge) and BK (Berkeley) were acquired from Agriculture Canada, ADRI (Nepean). Upon testing these against a few stock cultures of Brucella, it was found they were lytic for *B. abortus* 30, *B. suis* 144, weakly for *B. abortus* 2308, and apparently not lytic for *B. melitensis* 16M. The WB1 bacteriophage appeared to be more lytic than the BK bacteriophage. The ELVirA does not depend on lysis of the bacterial host by a bacteriophage. Indeed, some bacteriophages may not be able to infect, replicate or lyse their host (e.g., for the latter, Phi-X does not lyze its *E. coli* host but extrudes its progeny from the living cell) but may still attach sufficiently to give a positive ELVirA reading. The reason the inventors focused on a sensitive bacterial host (*B. abortus* 30) and lytic bacteriophage (WB1) was so that the latter's production and viability could be quantitated by means of plaque forming units (PFU).

Two methods are described for the production of WB1. The first method added the bacteriophage to a logarithmic growth of bacteria, the latter added these to a concentrated suspension of bacteria in a buffer that enhanced attachment. Although the final yields were similar, $3.2\times10^7$ and $5\times10^7$ PFU/ml respectively, the cells for the latter had a digested mucoid appearance and after centrifugation the supernatant had a thicker consistency. It is likely that the latter method was far superior for phage production but that filtration to remove the pathogenic bacterium had resulted in loss of phages. Table 1 illustrates examples of such losses. The counts of eluded phages when the filtrate was diluted then refilered through a 0.22 um membrane are listed in Table 1.

TABLE 1

Plaque forming units of a WB1 suspension that was refiltered through a 0.22 um membrane and plated onto *B. abortus* 30.

| Fraction (0.1 ml) | PFU |
|---|---|
| 1 | 146 |
| 2 | 129 |
| 3 | 44 |
| 4 | 26 |
| 5 | 3 |
| 6 | 3 |
| 7 | 0 |
| 8 | 0 |

It is evident that the phages in the preparation are binding to the membrane, reducing its pore size and hence restricting the number than can elute. Suggested ways by which the yield of bacteriophage can be increased include:

increase bacterial lysis (i.e. add enzymes such as lysozyme shortly before phage harvest, heat stress the culture at 42° C., test the use of mild detergents or low concentrations of organic solvents, alter the pH) to liberate more phage.

reduce the stickiness of the bacteriophage preparation (i.e. the supernatant from centrifuged culture) by the addition of enzymes (lysozyme, nucleases, lipases) before filtration.

sterilize the preparation without filtration (e.g. 0.3% chloroform, 0.5% phenol).

For the partial purification of WB1, both the polyethylene glycol precipitation method and the lyophilization-dialysis method were used to show that this can be accomplished by more than one means and still have viable bacteriophage. Other possible method for purification of phage include ammonium sulfate precipitation or altering the pH to a precipitation point.

For the final purification of WB1, a cesium chloride step-gradient was used and the phage band was found on top of the B layer (density 1.5). Cesium chloride is costly and the procedure, although it is efficient (160-fold purification) purifies only small amounts of phage in a time consuming process.

Despite the preliminary stage of bacteriophage purification, the inventors did produce sufficient amounts for the indirect (sandwich) ELVirA. The test was severely limited for:

because the coating of the microtiter plate used a stock of antigen prepared from *B. abortus* strain 2308, not strain 30, it is likely from the above observation that WB1 would have poor affinity for this bacterium due to time constraints, mice were immunized with a partially purified bacteriophage preparation (only 0.6% pure)

crude polyvalent sera and not purified antibodies to WB1 were used.

Upon testing the assay (4 h at 37° C.) the results were as set out in Table 2.

TABLE 2

| The Indirect (Sandwich) Enzyme-Linked Viral Assay (ELVirA) using unconjugated WB1 | |
|---|---|
| Antigen (50 ug/ml) | $A_{595\ nm}$ |
| *B. abortus* 2308 | 4.000 |
| *B. melitensis* 16M | 0.465 ± 0.068 |
| *F. tularensis* LVS | 1.066 ± 0.054 |
| *E. coli* 1511 | 0.194 ± 0.046 |
| Control (no bacteria) | 0.124 ± 0.004 |

That bacteriophage WB1 is specific for the "A" antigen of *B. abortus* is evident by the strong reaction with *B. abortus* 2308 but not *B. melitensis* 16M which has the "M" antigen. There was a weak interaction with *F. tularensis* (which was previously named *Brucella tularensis*) and this is consistent with the inventors' observation that the two organisms cross-react with antisera raised to the other. The lack of reaction with *E. coli* or the control show that the Indirect ELVirA can be used to detect pathogens.

For the Direct ELVirA, the 1 and 2-step glutaraldehyde methods and the MBS method to show that more than one conjugation technique is available for linking an enzyme (in this case urease) to a bacteriophage. However, the final results show that the tests do not give similar results. The 2-step glutaraldehyde method produced an inactive conjugate. Initially the 1-step glutaraldehyde method appeared to form an inactive conjugate as well, but when it was digested with lysozyme, RNase and DNase (each 20 ug/ml), the conjugate gave a colour reaction in all wells. At the time only partially purified bacteriophage WB1 was used Upon conjugating anti-Brucella monoclonal antibody Ys-T9-2 by the various methods, the MBS procedure appeared superior, and accordingly was applied to purified bacteriophage WB1. The WB1 (1 ug/ml) was activated with MBS and then reacted with urease. Upon testing for 30 min at 37° C., the results were as follows:

TABLE 3

| Direct Enzyme-linked Viral Assay (ELVirA) using urease conjugated WB1 bacteriophage | |
|---|---|
| Antigen (5 ug/ml) | $A_{595\ nm}$ |
| *B. abortus* 2308 | 2.315 ± 0.617 |
| *B. melitensis* 16M | 1.280 ± 0.155 |
| *F. tularensis* LVS | 1.627 ± 0.104 |
| *E. coli* 1511 | 1.701 ± 0.060 |
| control (no bacteria) | 0.156 ± 0.009 |

Table 3 shows that urease can be linked to a bacteriophage and that the conjugate can be used in a diagnostic assay.

The embodiments of the invention in which an exclusive property or privilege is claimed are defined as follows:

1. A method of detecting the presence of a bacteria in a sample comprising the steps of:

(a) producing a conjugate comprising a wild type bacteriophage specific to said bacteria directly linked to an enzymatically active enzyme;

(b) adding said conjugate to said sample to selectively bind said conjugate to said bacteria; and (c) detecting the presence of said bacteria by adding a substrate to said sample to generate a detectable change resulting from an enzymatic reaction between said enzyme and substrate.

2. A method of claim 1, wherein said bacteriophage is a Brucella bacteriophage.

3. A method of claim 1, wherein said bacteria is *Brucella abortus.*

4. A method of claim 1, wherein said enzyme is urease.

5. A method of claim 1, wherein the conjugate in step (a) is produced by adding a coupling agent to directly link said wild type bacteriophage to said enzyme.

6. A method of claim 5, wherein said coupling agent is m-maleimidobenzoyl-N-hydroxysuccinimide.

7. A method of claim 1, further comprising initially preparing a wild type bacteriophage stock to be utilized in the production of said conjugate comprising the steps of:

(a) adding a fresh culture of said bacteria to a buffer to enhance the bacteria susceptibility to infection by said wild type bacteriophage;

(b) infecting said bacteria with said wild type bacteriophage and allowing said wild type bacteriophage to proliferate;

(c) separating said wild type bacteriophage from said bacteria; and (d) obtaining said wild type bacteriophage stock containing wild type bacteriophages, wherein said wild type bacteriophages are utilized in the production of said conjugate.

8. A method of claim 7, wherein said buffer is maintained at a pH of 7.5.

9. A method of detecting the presence of a pathogenic bacteria in a sample comprising the steps of:

(a) producing a conjugate comprising a bacteriophage specific to said pathogenic bacteria directly linked to an enzymatically active enzyme;

(b) adding said conjugate to said sample to selectively bind said conjugate to said pathogenic bacteria; and (c) detecting the presence of said pathogenic bacteria by adding a substrate to said sample to generate a detectable change resulting from an enzymatic reaction between said enzyme and substrate.

10. A method of claim 9, wherein said bacteriophage is a Brucella bacteriophage.

11. A method of claim 9, wherein said bacteria is *Brucella abortus.*

12. A method of claim 9, wherein said enzyme is urease.

13. A method of claim 9, wherein the conjugate in step (a) is produced by adding a coupling agent to directly link said bacteriophage to said enzyme.

14. A method of claim 13, wherein said coupling agent is m-maleimidobenzoyl-N-hydroxysuccinimide.

15. A method of claim 9, further comprising initially preparing a bacteriophage stock to be utilized in the production of said conjugate comprising the steps of:

(a) adding a fresh culture of said pathogenic bacteria to a buffer to enhance said live, pathogenic bacteria susceptibility to infection by said bacteriophage;

(b) infecting said pathogenic bacteria with said bacteriophage and allowing said bacteriophage to proliferate;

(c) separating said bacteriophage from bacterial cells; and (d) obtaining said bacteriophage stock containing bacteriophages, wherein said bacteriophages are utilized in the production of said conjugate.

16. A method of claim 15, wherein said buffer is maintained at a pH of 7.5.

17. A method of detecting a bacteria in a sample containing said bacteria and other microorganisms, said method comprising the steps of:

(a) directly linking a bacteriophage specific to said bacteria to an enzymatically active enzyme to generate a bacteriophage-enzyme conjugate;

(b) adding said bacteriophage-enzyme conjugate to said sample to selectively attach said bacteriophage-enzyme conjugate to said bacteria;

(c) removing any unbound bacteriophage-enzyme conjugate and microorganism from said sample; and (d) adding a substrate to said sample, wherein said substrate is capable of promoting a detectable change with said enzyme to thereby enable detection of said bacteria attached to said bacteriophage-enzyme conjugate.

18. A method of claim 17, wherein said bacteriophage is a Brucella bacteriophage.

19. A method of claim 17, wherein said bacteria is *Brucella abortus*.

20. A method of claim 17, wherein said enzyme is urease.

21. A method of claim 17, wherein the conjugate in step (a) is produced by adding a coupling agent to directly link said bacteriophage to said enzyme.

22. A method of claim 21, wherein said coupling agent is m-maleimidobenzoyl-N-hydroxysuccinimide.

23. A method of claim 17, further comprising initially preparing a bacteriophage stock to be utilized in the production of said conjugate comprising the steps of:

(a) adding a fresh culture of said bacteria to a buffer to enhance the bacteria susceptibility to infection by said bacteriophage;

(b) infecting said bacteria with said bacteriophage and allowing said bacteriophage to proliferate;

(c) separating said bacteriophage from bacterial cells; and (d) obtaining said bacteriophage stock containing bacteriophages, wherein said bacteriophages are utilized in the production of said conjugate.

24. A method of claim 23, wherein said buffer is maintained at a pH of 7.5.

* * * * *